United States Patent
Lee et al.

(10) Patent No.: US 11,177,036 B2
(45) Date of Patent: Nov. 16, 2021

(54) INVENTORY MANAGEMENT THROUGH IMAGE AND DATA INTEGRATION

(71) Applicant: TRUEVIEW LOGISTICS TECHNOLOGY LLC, Oakland, MI (US)

(72) Inventors: Eric M. Lee, Oakland, MI (US); Thomas Hennel, South Bend, IN (US); Thomas Higginbotham, Fort Wayne, IN (US)

(*) Notice: Subject to any disclaimer, the term of this patent is extended or adjusted under 35 U.S.C. 154(b) by 403 days.

(21) Appl. No.: 16/229,396

(22) Filed: Dec. 21, 2018

(65) Prior Publication Data
US 2019/0198161 A1   Jun. 27, 2019

Related U.S. Application Data

(60) Provisional application No. 62/609,584, filed on Dec. 22, 2017.

(51) Int. Cl.
*G06K 9/00*   (2006.01)
*G06K 7/10*   (2006.01)
(Continued)

(52) U.S. Cl.
CPC ......... *G16H 40/20* (2018.01); *G06K 7/10297* (2013.01); *G06K 7/1413* (2013.01);
(Continued)

(58) Field of Classification Search
CPC .......... G06Q 30/0633; G06K 7/10722; G06K 7/1478; G06K 7/14
(Continued)

(56) References Cited

U.S. PATENT DOCUMENTS 8,933,935 B2   1/2015   Yang et al.
9,594,877 B2   3/2017   Kaula et al.
(Continued)

FOREIGN PATENT DOCUMENTS

EP   2092469   8/2009

OTHER PUBLICATIONS

Grand View Research, Augmented Reality (AR) & Virtual Reality (VR) in Healthcare Market Analysis By Component (Hardware, Software, and Service), By Technology (Augmented Reality, Virtual Reality), And Segment Forecasts, 2014-2025, Published May 2017, pp. 1-15, www.grandviewresearch.com.
(Continued)

*Primary Examiner* — Edwyn Labaze
(74) *Attorney, Agent, or Firm* — Heslin Rothenberg Farley & Mesiti P.C

(57) ABSTRACT

In a computer-implemented method, a computer program product, and a system, at least one processor obtains and decides a signal of decodable indicia to obtain information identifying an object made up of items. The processor obtains data comprising descriptive text characterizing the portion of the object, including quantitative inventory data related to the portion of the object. The processor displays the visual representation as a three dimensional image and the descriptive text, via an AR/VR device, generating a virtual projection in three dimensional space in a range of view of a user utilizing the device. The processor obtains a designation of a region in the visual representation and executes an action that changes a quantitative or a qualitative element of the descriptive text for an item represented by the region. The processor updates the descriptive text in the visual representation, to reflect the change.

17 Claims, 7 Drawing Sheets

(51) Int. Cl.
  *G06Q 10/08* (2012.01)
  *G06K 7/14* (2006.01)
  *G06Q 30/06* (2012.01)
  *G16H 40/20* (2018.01)

(52) U.S. Cl.
  CPC ....... *G06K 9/00671* (2013.01); *G06Q 10/087* (2013.01); *G06Q 30/0633* (2013.01)

(58) Field of Classification Search
  USPC ............. 705/26.8, 26.1; 235/462.11, 462.24, 235/462.41
  See application file for complete search history.

(56) References Cited

U.S. PATENT DOCUMENTS

| | | | |
|---|---|---|---|
| 2009/0112538 A1 | 4/2009 | Anderson et al. | |
| 2011/0098056 A1* | 4/2011 | Rhoads | G06K 9/4671 455/456.1 |
| 2016/0132046 A1* | 5/2016 | Beoughter | G05B 19/4184 700/17 |
| 2016/0188943 A1* | 6/2016 | Franz | G06Q 20/203 705/21 |
| 2016/0232498 A1* | 8/2016 | Tomlin, Jr. | G06Q 30/0206 |
| 2017/0186157 A1 | 6/2017 | Boettger et al. | |

OTHER PUBLICATIONS

Dr. Michael Gerards, Virtual Reality Applications in Healthcare and Medicine, Healthcare Shapers, Gunther Illert, Germany 2017, pp. 1-6.

* cited by examiner

INVENTORY MANAGEMENT THROUGH IMAGE AND DATA INTEGRATION

CROSS REFERENCE TO RELATED APPLICATION

This application claims priority to U.S. Provisional Application No. 62/609,584 filed Dec. 22, 2017, entitled, "INVENTORY MANAGEMENT SYSTEM AND METHOD," which is incorporated herein by reference in its entirety.

FIELD OF INVENTION

The invention relates generally to an inventory management and control system designed specifically to model and visualize data for use in enhancing and optimizing various processes utilized in the healthcare industry. However, the system and methods described are adaptable across additional industries.

BACKGROUND OF INVENTION

Today, healthcare providers of healthcare products often do not have visibility to these products once they leave the manufacturing facility, thereby creating significant inefficiencies and increased costs in the marketplace. Both users and providers lack technologies that reduce human error in identifying and counting inventory in a way that minimizes contamination while improving efficiency. This lack of inventory control equates to but is not limited to the following industry waste: 1) very low inventory turns equating to millions of dollars in working capital waste; 2) high risk of expiration in the field, creating risk that healthcare products could be surgically implanted or dispensed in or to the human patient; 3) costly recall or field action management, as inventory location is unknown once the product is shipped from the point of manufacture, and 4) an inventory supply/distribution chain that is filled with un-necessary inventory, thereby driving the cost of product and product management up significantly and 5) limited or non-existent statistical tracking of utilization of product while deployed at a facility.

One of the inefficiencies in inventory management is the process of recording inventory utilizing computer-readable indicia, such as bar codes and reading these codes with hand-held computing devices. Bar codes on the outside of inventory packages are encoded indicia that reflect can be used to reflect original equipment manager (OEM) name, part number, lot and/or serial number, quantity, utilization, and/or expiration date. Scanning bar codes on the outside of packaging using a handheld scanning device can be time-consuming and introduces possibilities of user error when indicia are skipped.

SUMMARY OF INVENTION

Shortcomings of the prior art are overcome and additional advantages are provided through the provision of a method for visualizing and modeling data to manage inventory. The method includes: obtaining, by one or more processors, a signal of decodable indicia; decoding, by the one or more processors, the signal of decodable indicia to access decoded data, wherein the decoded data comprises information identifying an object, wherein the object comprises a plurality of items; based on the information identifying the object, obtaining, by the one or more processors, from a memory, a visual representation of a portion of the object, wherein the visual representation is divided into a plurality of regions and each region represents an item of the plurality of items; based on identifying the object, obtaining, by the one or more processors, data comprising descriptive text characterizing the portion of the object, wherein the descriptive text comprises quantitative inventory data related to the portion of the object; displaying, by the one or more processors, the visual representation as a three dimensional image and the descriptive text, via a device, wherein the device is selected from the group consisting of: an augmented reality device and a virtual reality device, wherein the three dimensional image comprises a virtual projection in three dimensional space in a range of view of a user utilizing the device, wherein the device comprises a user interface; obtaining, by the one or more processors, via the user interface, a designation of at least one of the plurality of regions in the visual representation; based on obtaining the designation, executing an action, wherein the action changes a quantitative or a qualitative element of the descriptive text for an item represented by the at least one of the plurality of regions; and updating, by the one or more processors, concurrently with the executing, the descriptive text in the visual representation to reflect the changed quantitative or qualitative element.

Shortcomings of the prior art are overcome and additional advantages are provided through the provision of a system for visualizing and modeling data to manage inventory. The system includes, for example, a memory, one or more processors in communication with the memory, a device (selected from the group consisting of: an augmented reality device and a virtual reality device) communicatively coupled to the one or more processors, program instructions executable by the one or more processors via the memory to perform a method, the method comprising: obtaining, by the one or more processors, a signal of decodable indicia; decoding, by the one or more processors, the signal of decodable indicia to access decoded data, wherein the decoded data comprises information identifying an object, wherein the object comprises a plurality of items; based on the information identifying the object, obtaining, by the one or more processors, from a memory, a visual representation of a portion of the object, wherein the visual representation is divided into a plurality of regions and each region represents an item of the plurality of items; based on identifying the object, obtaining, by the one or more processors, data comprising descriptive text characterizing the portion of the object, wherein the descriptive text comprises quantitative inventory data related to the portion of the object; displaying, by the one or more processors, the visual representation as a three dimensional image and the descriptive text, via the device, wherein the three dimensional image comprises a virtual projection in three dimensional space in a range of view of a user utilizing the device, wherein the device comprises a user interface; obtaining, by the one or more processors, via the user interface, a designation of at least one of the plurality of regions in the visual representation; based on obtaining the designation, executing an action, wherein the action changes a quantitative or a qualitative element of the descriptive text for an item represented by the at least one of the plurality of regions; and updating, by the one or more processors, concurrently with the executing, the descriptive text in the visual representation to reflect the changed quantitative or qualitative element.

Computer systems, computer program products and methods relating to one or more aspects of the technique are also described and may be claimed herein. Further, services relating to one or more aspects of the technique are also described and may be claimed herein.

Additional features are realized through the techniques of the present invention. Other embodiments and aspects of the invention are described in detail herein and are considered a part of the claimed invention.

BRIEF DESCRIPTION OF DRAWINGS

The foregoing and objects, features, and advantages of one or more aspects of the invention are apparent from the following detailed description taken in conjunction with the accompanying drawings in which.

DETAILED DESCRIPTION OF THE INVENTION

Figure 1:
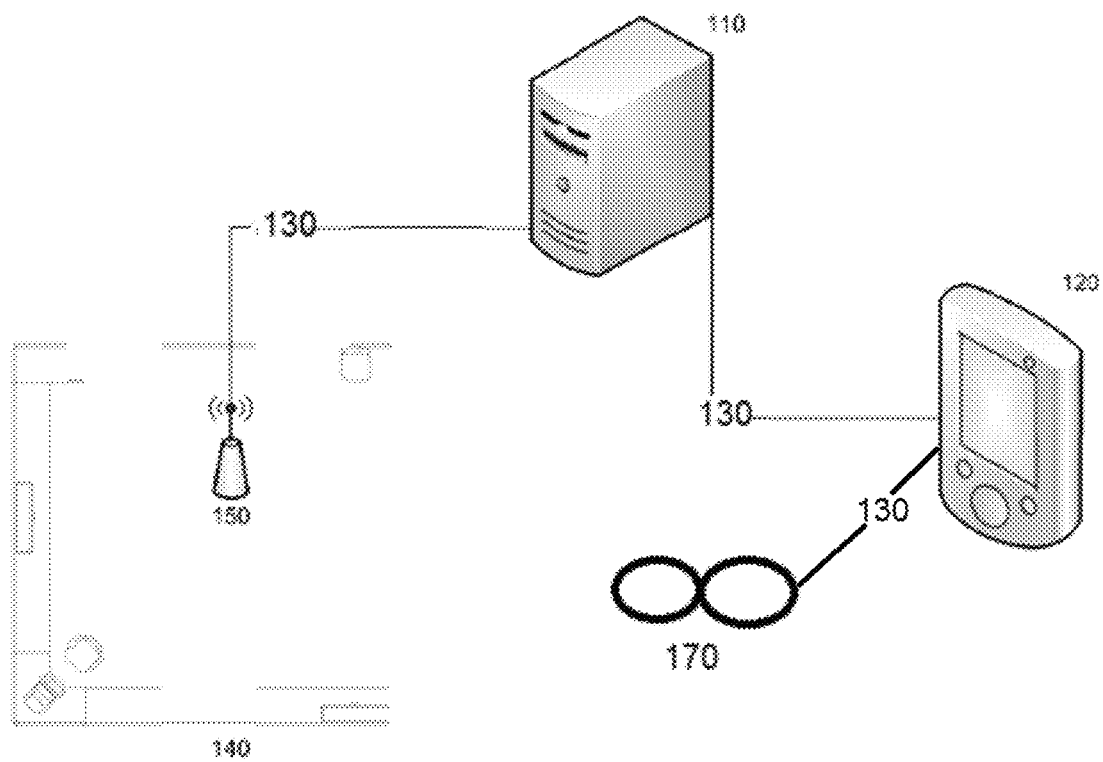
FIG. 1 is an example of a technical architecture that can be utilized by embodiments of the present invention.

Aspects of the present invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure.

Embodiments of the present invention significantly improve the ability of consumers to manage inventory as well as to generate visuals of the inventory and provide real-time information to individuals making decisions regarding inventory. Aspects of the present invention perform an improved service offering (greater functionality, greater information visibility, improved accuracy, improved business decision making) at a much lower cost than the current industry solution for industries, including but not limited to, the medical and healthcare industry. In addition to financial efficiency, embodiments of the present invention enable real-time re-ordering and real-time data capture and visualization, to increase the technical efficiencies of embodiments of the present invention.

Embodiments of the present invention are inextricably tied to computing and provide significantly more than existing inventory management and product realization (real-time lookup and comprehension and application of data) approaches. Embodiments of the present invention are inextricably tied to computing based on their reliance on and utilization of computing devices, such as virtual reality and augmented reality interfaces, in order to provide visualizations to users and allow users to comprehend and manipulate data related to inventory management, in real-time. Additionally, the interconnectivity of the augmented reality and virtual reality devices to various databases across differing inventory management systems, and to other relevant medical and healthcare databases enables the diversity of the functionality. The interconnectivity is enabled by communications over computing networks. Embodiments of the present invention are also inextricably linked to computing because various aspects are directed to enhancing a user interfaces utilized to interact with the program code executing on one or more processors.

Embodiments of the present invention provide significantly more than existing approaches to inventory management and comprehensive data capture and visualization related to data capture by providing a hands free, wearable augmented or virtual reality system that provide visibility to inventory to a user. Users can include, but are not limited to inventory providers, manufacturers, and/or clinicians. Additionally, embodiments of the present invention are not limited, like existing systems, to receiving inputs via barcode scanning, alone. In embodiments of the present invention, various aspects enable program code executing on one or more processing devices to obtain data via visual inputs, such as bar codes, form factors, color, and/or electromagnetic spectrum indicia including but not limited to radio-frequency identification (RFID), near-field communication NFC, and/or passive WiFi. Additionally, embodiments of the present invention include aspects that are highly portable and therefore, can be utilized in a variety of different environments.

Aspects of embodiments of the present invention enable users, including but not limited to, health care product providers and/or Original Equipment Manufacturers (OEMs) the ability of making inventory or objects in the field highly visible. In some embodiments of the present invention, based on this visibility, a user can manipulate the objects in order to complete tasks including but not limited to, obtaining additional information about the objects and/or ordering additional objects. Visibility means that an authorized individual utilizing the present invention can locate or report on inventory or objects at any location or stocking location serviced for which there is data available on a memory resources accessible to the system. This functionality enables a single entity to manage the inventory or objects across multiple physical locations because the inventory or item at each location is "visible." The term OEM refers to original manufacturers of products or components that are purchased or consigned by another company and retailed under that purchasing company's brand name. The term OEM refers to the company that originally manufactured the product.

Embodiments of the present invention can include, but are not limited to: 1) an inventory management and control system; 2) a wearable and/or hand-held, electronic data capture hardware and software system with advanced image recognition and indicia scanning and reading capabilities; 3) an augmented and/or virtual reality device that is utilized by program code in embodiments of the present invention to provide an interface for users; and 4) one or more programs comprising an application programming interface (API) that handles communications between the inventory management system and the wearable device. In some embodiments of the present invention, the wearable device that produces the AR/VR interface for the user also includes the advanced indicia identification capabilities. The wearable device can also include an off-the-shelf AR/VR user interface, including but not limited to, commercially available products, such as those manufactured by Oculus.

As discussed above, in some embodiments of the present invention, both visual capabilities and data capture capabilities are integrated into the wearable device. The wearable device can also include more than one distinct device, communicatively coupled, in order to display the inventory as well as obtain data related to the inventory. The inventory management system can be a proprietary system and/or a third party system. Thus, the API can broker communications between the inventory management system and the AR/VR device, such that the API obtains data from the inventory management system, displays data in an original manner utilizing the advantages of the AR/VR device, in the interface of the AR/VR device, and obtains inputs from the user via the AR/VR device, in order to take actions related to the displayed inventory item(s). These actions can include, but are not limited to: 1) generating an order request for an item represented in the AR/VR simulation/visualization created by the program code executing on the device; 2) counting inventory for an item represented in the AR/VR simulation/visualization created by the program code executing on the device; 3) triggering a recall of an item represented in the AR/VR simulation/visualization created by the program code executing on the device; and/or 4) triggering a search in the one or more designated databases for additional data to supplement the descriptive text (generated by the program code and also displayed in the interface) related to an item represented in the AR/VR simulation/visualization created by the program code executing on the device.

In an embodiment of the present invention, the gathering of inventory or item information can be accomplished by utilizing a AR/VR computing device, including what is referred to, generally, herein, as an encoded information reading (EIR) terminal, configured to read bar codes and/or other types of encoded information, to scan indicia, including but not limited to, bar codes, RFID, NFC and/or Passive WiFi on the packaging of items. Encoded indicia on packages can be used to reflect original equipment manager (OEM) name, part number, lot and/or serial number, quantity, and/or expiration date or other data. As discussed earlier, individually scanning bar codes on the outside of packaging using a handheld scanning device can be time-consuming and introduces possibilities of user error when indicia are skipped. Thus, another advantage embodiments of the present invention offer over existing approaches to inventory management is that in some embodiments of the present invention, the aforementioned mobile device can be utilized to scan a group of items at one time by utilizing software and/or hardware to capture an image of a display of inventory or items and extract bar codes and/or other encoded indicia from the image and provide a visualization of data retrieved from a coupled data source, based on the scanning, via augmented reality devices. In some embodiments of the present invention, the method further includes utilizing software and/or hardware to decode the extracted bar codes or other information, and to retain the decoded information. The retained information assists in managing the inventory or items, both on the particular augmented display and/or at different locations.

FIG. 1 is an example of an architecture 100 that can be utilized by embodiments of the present invention. At least on computer server 110 with at least one processor executes program code as part of an inventory management and control system. In some embodiments of the present invention, the at least one server 110 is one or more resources of a cloud computing system and/or other shared or distributed computing system. In some embodiments of the present invention, the program code provides the described functionality as a service to subscribers to the shared computing system. This program code is also referred to as software as well as one or more programs throughout this disclosure.

Memory resources on the computer server 110 and and/or in communication with the program code execute on the server and can also comprise part of an inventory management and control system. The server 110 communicates with at least one mobile computing device 120, including but not limited to, an encoded information reading (EIR) terminal, including but not limited to an AR/VR device 170, configured to read bar codes and/or other types of encoded information and to provide an AR/VR display and interface to enable a user to interact through this interface. In an embodiment of the present invention, the mobile computing device 120 comprises an EIR terminal with image recognition and bar code scanning and electronic indicia reading capabilities, which are utilized, in an embodiment of the present method, for accurately inventorying healthcare products, including but not limited to, medical devices. (As explained earlier, enhanced inventory management as it pertains to the healthcare industry is discussed through to provide a non-limiting and concrete example of the applicability of aspects of the present invention to a particular field. However, as understood by one of skill the art, aspects of some embodiments of the present invention can be implemented across other industries to enable enhanced inventory visualization and management.)

In FIG. 1, the server 110 can communicate with the mobile computing device 120 over a communications connection 130. The AR/VR device 170 can similarly communicate with the mobile computing device 120 over a communications connection 130. As understood by one of skill in the art, the EIR reading capability, which in this example is integrated into the mobile computing device 120, can also be integrated into an AR/VR device 170. In embodiments of the present invention, AR/VR devices 170 include wearable, implanted, handheld, and/or stationary computing resources. In some embodiments of the present invention, a user can utilize one or more AR/VR devices 170 at the same time. Thus, in some embodiments of the present invention, the AR/VR device 170 has the dual function of capturing a signal of decodable indicia from an item and displaying data obtained about the item, to the user, based on decoding the signal. In some embodiments of the present invention, the program code obtains data related to an item, based on the appearance of the item (no decoding is done) and is able to display a visualization of the item in the AR/VR interface for manipulation by the user.

The at least one mobile computing device 120 may include an integrated and/or separate (as displayed in FIG. 1) augmented or virtual reality device 170. In embodiments of the present invention, the AR/VR device 170 superimposes an image (generated by the device and/or an external processor communicatively coupled to the device 170) on a user's view (in the field of view of the user in three dimensional space), and/or a display of a two dimensional and/or three dimensional image on the mobile computing device 120. Thus, the AR/VR device 170 provides a composite view. In embodiments of the present invention where the augmented or virtual reality device 170 is a virtual reality device, the AR/VR device 170 generates and displays a three-dimensional image/data or environment that can be interacted with by a user in a seemingly real or physical way. The device may comprise stationary and/or portable wearable/handheld electronic equipment. In embodiments of the present invention, the augmented or virtual reality device 170 can be wearable. In some embodiments of the present invention, a user interacts with the augmented or virtual reality device 170 through (user) interfaces in the devices or communicatively coupled to the devices, including but not limited to, a haptic feedback interface, a voice recognition and/or audio interface, a gesture recognition interface, and/or a biometric recognition interface.

As understood by one of skill in the art, embodiments of the present invention can be utilized in a variety of environments to determine inventory and/or provide interactive experiences to users with various items. One non-limiting example of an environment where aspects of the present invention can be implemented is in a physical space 140 (e.g., a secure room, a hospital, a physically or electronically bounded area) where a specific type of item is kept. Although represented as a single room in FIG. 1, the room 130 represents one to many rooms and/or spaces. These spaces can be physically or virtually defined. Within the space 140, one or more programs executing on a processing device, in an embodiment of the present invention can capture, including via RFID capture, inventory passing into the space 140 and inventory passing out of the space 140. To obtain this data, a user can utilize the reading capabilities of a wearable device of the present invention and/or the one or more programs can communicate with a device in the space 140, including but not limited to, an RFID reading devices 150 in the space 140. The data captured by the RFID reading devices 150 can be communicated electronically to the server 110. One or more devices within the space that the program code can communicate with can include Internet of Things (IoT) devices within the space both temporarily (e.g., worn by individuals who enter the space) or permanently situated in the space (e.g., environmental sensors).

In FIG. 1, the physical space 140 is given as an example of merely one source of data and one way in which the program code can delineate data obtained and utilized in inventory management. In embodiments of the present invention, the mobile computing device 120 and/or the AR/VR device 170 can obtain data about items managed and displayed by the AR/VR device 170 for comprehension and manipulation based on obtaining data from Internet of Things (IoT) devices, which are not necessarily constricted to a given physical setting. As understood by one of skill in the art, the Internet of Things (IoT) is a system of interrelated computing devices, mechanical and digital machines, objects, animals and/or people that are provided with unique identifiers and the ability to transfer data over a network, without requiring human-to-human or human-to-computer interaction. These communications are enabled by smart sensors, which include, but are not limited to, both active and passive radio-frequency identification (RFID) tags, which utilize electromagnetic fields to identify automatically and to track tags attached to objects and/or associated with objects and people. Smart sensors, such as RFID tags, can track environmental factors related to an object or an area, including but not limited to, temperature and humidity. The smart sensors can be utilized to measure temperature, humidity, vibrations, motion, light, pressure and/or altitude. IoT devices also include individual activity and fitness trackers, which include (wearable) devices or applications that include smart sensors for monitoring and tracking fitness-related metrics such as distance walked or run, calorie consumption, and in some cases heartbeat and quality of sleep and include smartwatches that are synced to a computer or smartphone for long-term data tracking. Because the smart sensors in IoT devices carry unique identifiers, a computing system that communicates with a given sensor can identify the source of the information. Within the IoT, various devices can communicate with each other and can access data from sources available over various communication networks, including the Internet. IoT devices can also be configured to communicate over private and/or secure networks with computing resources executing program code implementing aspects of some embodiments of the present invention. Additionally, certain IoT devices can also be placed at various locations and can provide data based in monitoring environmental factors at the locations. In some embodiments of the present invention device 150 can be understood as an IoT device at a given location, which can be accessed by one or more programs in an embodiment of the present invention in order to collect data related to items in the physical space 140.

Figure 2:
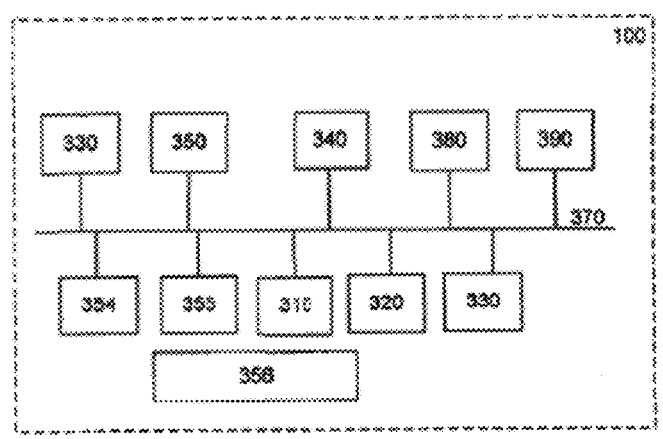
FIG. 2 is a component-level diagram of one embodiment of an EIR terminal, which is an example of a mobile computing device that can be utilized in an embodiment of the present invention with reading capabilities.

FIG. 2 is a component-level diagram of one embodiment of an EIR terminal, which is an example of a mobile computing device 120 or a component of a mobile computing device 120 and/or AR/VR device 170 that can be utilized in an embodiment of the present invention. As discussed above, the functionality of the EIR terminal in obtaining and decoding signals of decodable indicia can be integrated into the AR/VR device utilized to visualize the data. In the example of FIG. 2, the EIR terminal 100 can comprise at least one microprocessor 310 and a memory 320, both coupled to the system bus 370. The microprocessor 310 can be provided by a general purpose microprocessor or by a specialized microprocessor (e.g., an ASIC). In one embodiment, EIR terminal 100 can comprise a single microprocessor which can be referred to as a central processing unit (CPU). In another embodiment, EIR terminal 100 can comprise two or more microprocessors, for example, a CPU providing some or most of the EIR terminal functionality and a specialized microprocessor performing some specific functionality. A skilled artisan would appreciate the fact that other schemes of processing tasks distribution among two or more microprocessors are within the scope of this disclosure.

EIR terminal 100 can further comprise a communication interface 340 communicatively coupled to the system bus 370. In one embodiment, the communication interface can be provided by a wireless communication interface. The wireless communication interface can be configured to support, for example, but not limited to, the following protocols: at least one protocol of the IEEE 802.11/802.15/802.16 protocol family, at least one protocol of the HSPA/GSM/GPRS/EDGE protocol family, TDMA protocol, UMTS protocol, LTE protocol, and/or at least one protocol of the CDMA/1xEV-DO protocol family.

EIR terminal 100 can further comprise a keyboard interface 354 and a display adapter 355, both also coupled to the system bus 370. EIR terminal 100 can further comprise a battery 356. In one embodiment, the battery 356 can be provided by a replaceable rechargeable battery pack.

EIR terminal 100 can further comprise a GPS receiver 380. EIR terminal 100 can further comprise at least one connector (note pictured) configured to receive a subscriber identity module (SIM) card.

EIR terminal 100 can further comprise one or more EIR devices 330, provided, for example, but not limited to, by an RFID reading device, a bar code reading device, or a card reading device. In one embodiment, EIR terminal 100 can be configured to read an encoded message using EIR device 330, and to output raw message data containing the encoded message. In another embodiment, the EIR terminal 100 can be configured to read an encoded message using EIR device 330, and to output decoded message data corresponding to the encoded message. As used herein, "message" is intended to denote a character string comprising alphanumeric and/or non-alphanumeric characters. An encoded message can be used to convey information, such as identification of the source and the model of a product, for example, in a UPC code.

Mobile computing devices that read bar codes, read RFID, or read cards bearing encoded information can read more than one of these categories while remaining within the scope of this disclosure. For example, a device that reads bar codes may include a card reader, and/or RFID reader; a device that reads RFID may also be able to read bar codes and/or cards; and a device that reads cards may be able to also read bar codes and/or RFID. For further clarity, it is not necessary that a device's primary function involve any of these functions in order to be considered such a device; for example, a cellular telephone, smartphone, or PDA that is capable of reading bar codes is a device that read bar codes and can constitute a mobile computing device 120 and/or an AR/VR device 170, as seen in FIG. 1, for purposes of this disclosure.

In an embodiment of the present invention, the EIR terminal 100 includes a digital camera component 350, which enables the EIR terminal 100 to capture digital images, which may be processed by the one or more processing units of the EIR terminal 100. In embodiments of the present invention where the program code displays images and/or item data captured and/or decoded by the EIR terminal 100 on an interface of the AR/VR device (FIG. 1, 170). For example, as will be discussed later in greater detail, the GUI of the AR/VR device (FIG. 1, 170) can display to the operator that an item that was scanned by the EIR terminal 100 has expired and/or has been recalled.

In some embodiments of the present invention, the EIR terminal may include a display device 390, including but not limited to a virtual reality device and/or an augmented reality device. As discussed above, the EIR terminal and the display can also be separate and can be communicatively coupled. An API in embodiments of the present invention can broker communications between the AR/VR device and the EIR terminal. However, in embodiments of the present invention where the display and data collection and interpretation functionalities are integrated into a common device, as in FIG. 4, the display device 390 can generate a three dimensional image that the user can interact with in some capacity. For example, when the display device 390 includes an augmented reality device, the EIR terminal 300 generates an image and utilizes the device 390 to superimpose the image on a user's view of the real world, thus providing a composite view. As discussed herein, the composite view can also include data relevant to the item(s) being displayed to the user in the view. When the display device 370 includes a virtual reality device, the device 390 generates a simulation of a three-dimensional image/data or environment. The environment is perceived by the user as accepting inputs as the device 390 includes stationary and/or portable wearable/handheld electronic equipment that can receive inputs into the EIR device 300 based on the actions and movements of a user experiencing the virtual reality generated by the device 390. The device can provide the user with haptic feedback to indicate that an input provided through an action or a movement was accepted.

As aforementioned, in some embodiments of the present invention, rather than being internal to an EIR device 300, a virtual and/or augmented reality device is communicatively coupled to the EIR device 300. In embodiments such as these, while the virtual reality device can serve as an input device to the EIR terminal 300, the augmented reality device may enhance a display on the EIR device itself and a component of the EIR terminal 300 may accept input from a user on an input/output device of the EIR terminal 300 and/or communicatively coupled to the EIR terminal 300.

Figure 3:
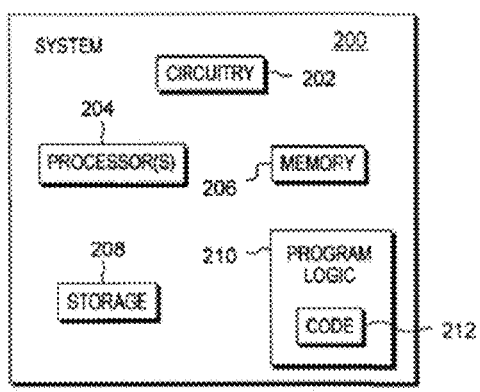
FIG. 3 illustrates a block diagram of a resource in a computer system, which is part of the technical architecture of certain embodiments of the technique.

FIG. 3 illustrates a block diagram of a resource 200, like server 110, in computer system 100, which is part of the technical architecture of certain embodiments of the technique. As aforementioned, the computing resources in embodiments of the present invention can be part of distributed or shared computing environments, including cloud computing environments. The resource 200 may include a circuitry 202 that may in certain embodiments include a microprocessor 204. The computer system 200 may also include a memory 206 (e.g., a volatile memory device), and storage 208. The storage 208 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 208 may comprise an internal storage device, an attached storage device and/or a network accessible storage device. The system 200 may include a program logic 210 including code 212 that may be loaded into the memory 206 and executed by the microprocessor 204 or circuitry 202.

In certain embodiments, the program logic 210 including code 212 may be stored in the storage 208, or memory 206. In certain other embodiments, the program logic 210 may be implemented in the circuitry 202. Therefore, while FIG. 2 shows the program logic 210 separately from the other elements, the program logic 210 may be implemented in the memory 206 and/or the circuitry 202.

Using the processing resources of a resource 200 to execute software, computer-readable code or instructions, does not limit where this code is can be stored. The terms program logic, code, and software are used interchangeably throughout this application.

Figure 4:
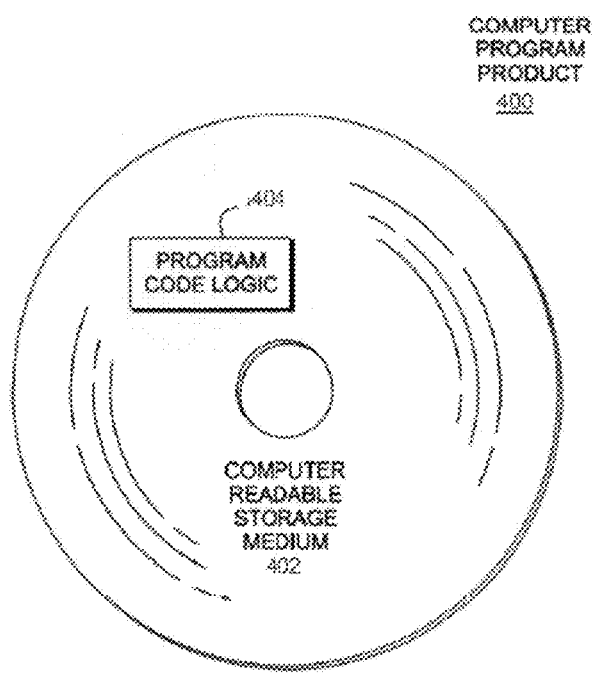
FIG. 4 is a computer program product that can execute program code to perform certain aspects of some embodiments of the present invention.

Referring to FIG. 4, in one example, a computer program product 400 includes, for instance, one or more non-transitory computer readable storage media 402 to store computer readable program code means or logic 404 thereon to provide and facilitate one or more aspects of the technique.

As will be appreciated by one skilled in the art, aspects of the technique may be embodied as a system, method or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the technique may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium or an augmented reality readable signal or storage medium. A computer readable signal medium may include a propagated data signal with computer readable program code embodied therein, for example, in baseband or as part of a carrier wave. Such a propagated signal may take any of a variety of forms, including, but not limited to, electromagnetic, optical or any suitable combination thereof. A computer readable signal medium may be any computer readable medium that is not a computer readable storage medium and that can communicate, propagate, or transport a program for use by or in connection with an instruction execution system, apparatus or device. A augmented reality medium may be a computer readable medium that can take a variety of forms and that is not a computer readable signal or storage medium with computer readable program code embodied therein that can communicate, propagate or transport a program for use by or in connection with an instruction execution system apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the technique may be written in any combination of one or more programming languages, including but not limited to an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices including augmented reality devices to function in a particular manner, such that the instructions stored in the computer readable medium produce an article of manufacture including instructions which implement the function/act specified in the flowchart and/or block diagram block or blocks.

The computer program instructions, also referred to as computer program code, may also be loaded onto a computer, other programmable data processing apparatus, or other devices including augmented reality devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block and system diagrams in FIGS. 1-7 and FIG. 9 illustrate the architecture, functionality, and operation of possible implementations of systems, methods and computer program products according to various embodiments of the technique. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the technique may be provided, offered, deployed, managed, serviced, etc. by a service provider who offers management of customer environments using augmented/virtual reality devices. For instance, the service provider can create, maintain, support, etc. computer code and/or a computer infrastructure that performs one or more aspects of the technique for one or more customers using augmented/virtual reality devices. In return, the service provider may receive payment from the customer under a subscription and/or fee agreement, as examples. Additionally or alternatively, the service provider may receive payment from the sale of advertising content to one or more third parties. Is payment usually addressed in a patent?

In one aspect of the technique, an application may be deployed for performing one or more aspects of the technique. As one example, the deploying of an application comprises providing computer infrastructure operable to perform one or more aspects of the technique.

As a further aspect of the technique, a computing infrastructure may be deployed comprising integrating computer readable code into a computing system, in which the code in combination with the computing system is capable of performing one or more aspects of the technique. As a further aspect of the technique, the system can operate in a peer to peer mode where certain system resources, including but not limited to, one or more databases, is/are shared, but the program code executable by one or more processors is loaded locally on each computer, including the AR/VR device 170 of FIG. 1.

As yet a further aspect of the technique, a process for integrating computing infrastructure comprising integrating computer readable code into a computer system may be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, augmented/virtual reality devices, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

As aforementioned, an embodiment of the present invention includes one or more mobile computing devices, such the augmented/virtual reality devices (e.g., FIG. 1, 170) either communicatively coupled to or integrated with an EIR terminal (e.g., FIG. 2). In an embodiment of the present invention, the mobile computing device is a wearable or hand-held, electronic data capture system with advanced image recognition and/or bar code, RFID, NFC, Passive WiFi, scanning and reading capabilities for accurately identifying items, including but not limited to, counting healthcare products. In some embodiments of the present invention, the mobile computing device may be a virtual reality device and/or many be communicatively coupled to an augmented reality device. The virtual reality or augmented reality device may be utilized to provide users with visuals that are immersive and three dimensional and in some cases, enable the users to interact with the virtual representation through movement and/or voice commands. In some embodiments of the present invention, the user may be alerted to the acceptance of inputs by the system through haptic feedback experienced via the augmented reality device or the virtual reality device.

One non-limiting example for use of aspects of some embodiments of the present invention is to order specific items from a collection of items. This non-limiting example is provided for illustrative purposes, only. In some embodiments of the present invention, the aforementioned device interfaces with an inventory management system, also understood as a data manager to support inventory management and inventory replenishment of products, including but not limited to, healthcare products and/or medical devices. In an embodiment of the present invention, the program code executed by a processing resource on the mobile device is configured for use in the medical device and/or healthcare industries. Among the software features customized for this industry is the capability to select areas on an image of a device tray, where small, un-marked parts would be positioned and create a replenishment order based on this selection. In order to utilize this feature, a user can utilize the EIR capabilities of the mobile device to scan a barcode and/or an RFID or other readable indicia and/or capture an image that can be recognized by the program code. After making this selection, program code executing either on the device and/or at the server decodes this identification information to recognize the item that was scanned. In this example, the scanned item comprises a group of trays containing many small items. After identifying the item scanned, the program code renders a visual in a manner that provides a user with a three dimensional and potentially interactive view of each tray of the device. The program code utilizes the unique features of the AR/VR device (e.g., FIG. 1, 170), to render the item in a composite view, which is discussed herein in FIG. 7.

In some embodiments of the present invention, the one or more programs may renders the visual through a graphical user interface (GUI) on the mobile device. Rather than view the visual directly in the GUI, the user utilizes an augmented reality device (e.g., a wearable device) to view a three dimensional representation of each tray. The augmented reality device overlays a three dimensional visual on the GUI, which is visible to a user who wears the augmented reality device. In some embodiments of the present invention, only the augmented reality device and not the GUI render the visual. In some embodiments of the present invention, the mobile device is communicatively coupled to a virtual reality device or includes an embedded virtual reality device. In these embodiments, the virtual reality device not only renders a three dimensional image, the device also includes inputs that receive commands from the user, related to the image. For example, the virtual reality device may include sensors that track the user's movement and interpret certain movements as certain inputs. Upon acceptance of the inputs, the virtual reality device may provide the user with haptic feedback.

Returning to the non-limiting example, viewing the visual, the user compares the images of the trays to the actual trays and selects the regions on the image that represent missing items in the trays. The user may select the missing items through a GUI, but while viewing the augmented image, or by making movements or reciting voice commands that are interpreted as specific inputs by the virtual reality device. Acceptance of the inputs may be indicated through the generation of haptic feedback by the device. The user selections are communicated from the mobile device to the data manager on the server and the data manager can then determine how many pieces there should be located in that storage slot and will issue a replenishment order for the missing number of pieces.

Embodiments of the present invention, including those embodiments that assist in managing inventory related, for example, to the medical industry, and, specifically, the healthcare industry, including but not limited to, the medical device industry, utilize images of kits in an interactive manner in order to assist in the replenishment of missing parts. Utilizing this technique, users (e.g., auditors) would select the items from the image that are missing from the kit by utilizing various input methods, including but not limited to, touching the item in the image, indicating the item with a voice command, and/or indicating the item with a specific gesture (e.g., taps, gestures, blink/tracking, facial and hand movements). As understood by one or skill in the art, a user of an AR/VR device can utilize existing interfaces in communicate with the program code. In an embodiment of the present invention, selecting elements of an image in the GUI would cause the program code to "Gray Out" the selected item or items in the (augmented and/or virtual) image. This graying of the product would signify that the item(s) were not present in the kit. The program code would then build the inventory list based upon the image, meta-data and user inputs.

Figure 5:
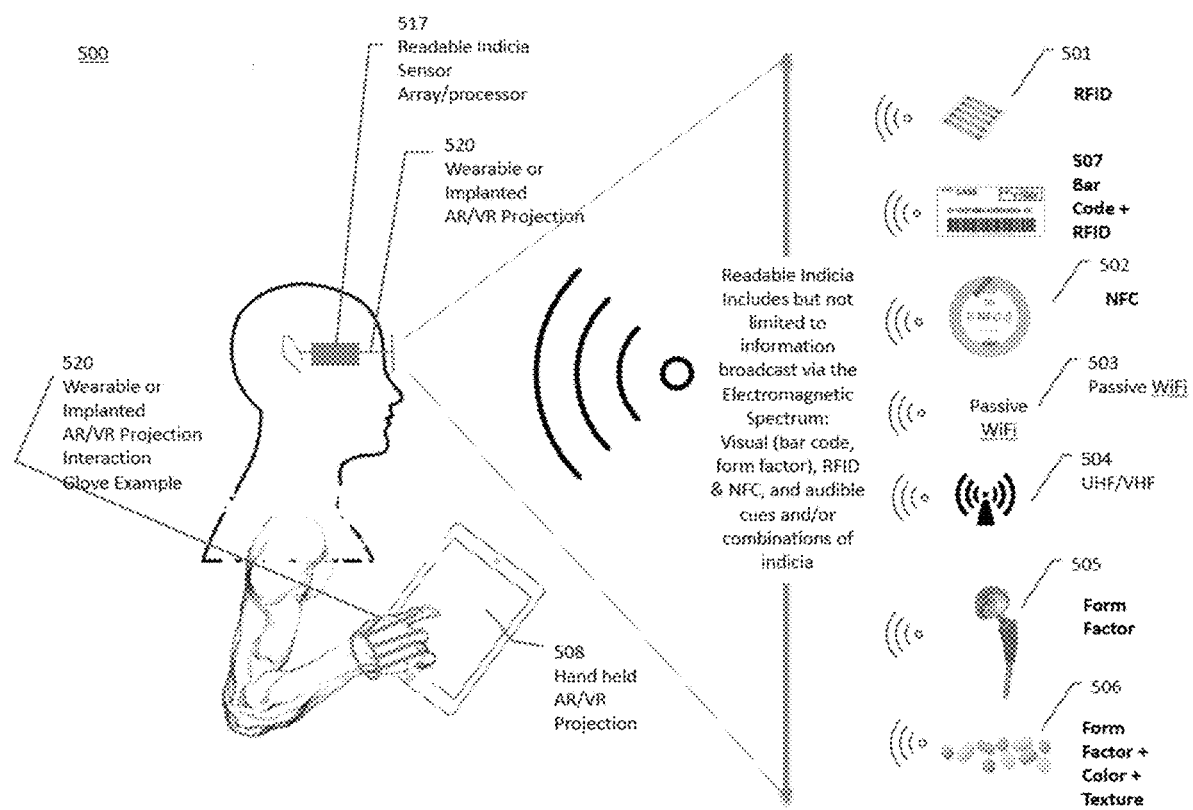
FIG. 5 is a technical environment into which aspects of some embodiments of the present invention can be integrated.

FIG. 5 is a technical environment 500 into which aspects of some embodiments of the present invention are integrated. FIG. 5 provides an example of how aspects of the present invention work together, within this technical environment 500, to collect data, interpret data, and manage inventory. As illustrated in FIG. 5, in some embodiments of the present invention, one or more programs executing on a processing device obtain, via an using augmented/virtual reality device 520 (illustrated in FIG. 5 as one or more of a wearable/implanted AR/VR projection component 520 and a wearable/implanted AR/VR glove 520) to capture visual representations and decodable indicia of inventory objects use program code executing of a processor to identify objects, recall data from memory related to these objects (and/or obtain data from external systems based on executing queries), load data from memory, and display selected data visually in the view of the user AR/VR device 520. In some embodiments of the present invention, the program code displays the additional data related to the item adjacent to or near the subject object to create a composite view of the real object and the virtually visualized relevant data.

As illustrated in FIG. 5, the program code identifies objects using a variety of signals and items of decodable indicia, and/or non-encoded characteristics, including but not limited to, RFID 501, a combination of a barcode and RFID 507, NFC 502, passive WiFi 503, UHF/VHF 504, form factor 505, and/or a combination of form factor, color, and texture 506. As indicated in FIG. 5, the readable indicia includes, but not limited to, information broadcast via the Electromagnetic Spectrum, such as: visual data (e.g., bar code, form factor), RFID, and NFC, and audible cues and/or combinations of indicia. The program code obtains this data via one or more AR/VR devices 520. As illustrated in FIG. 5, the AR/VR device 520 captures the indicia from utilizing a readable indicia sensor array/processor 517 that is either integrated into the AR/VR device 520, or communicatively coupled to the AR/VR device 520. The program code can project the image, which can include a real and/or virtual image of the object and data describing the object (based on utilizing the indicia to retrieve additional data from a data source), within a view of the user, as a projection 520, and/or as a handheld projection 508, on a computing device comprising the interface capable of the handheld projection 508. As discussed earlier, the user can interact with the projection utilizing a variety of interfaces and the interactions are obtained by the program code in embodiments of the present invention.

Figure 6:
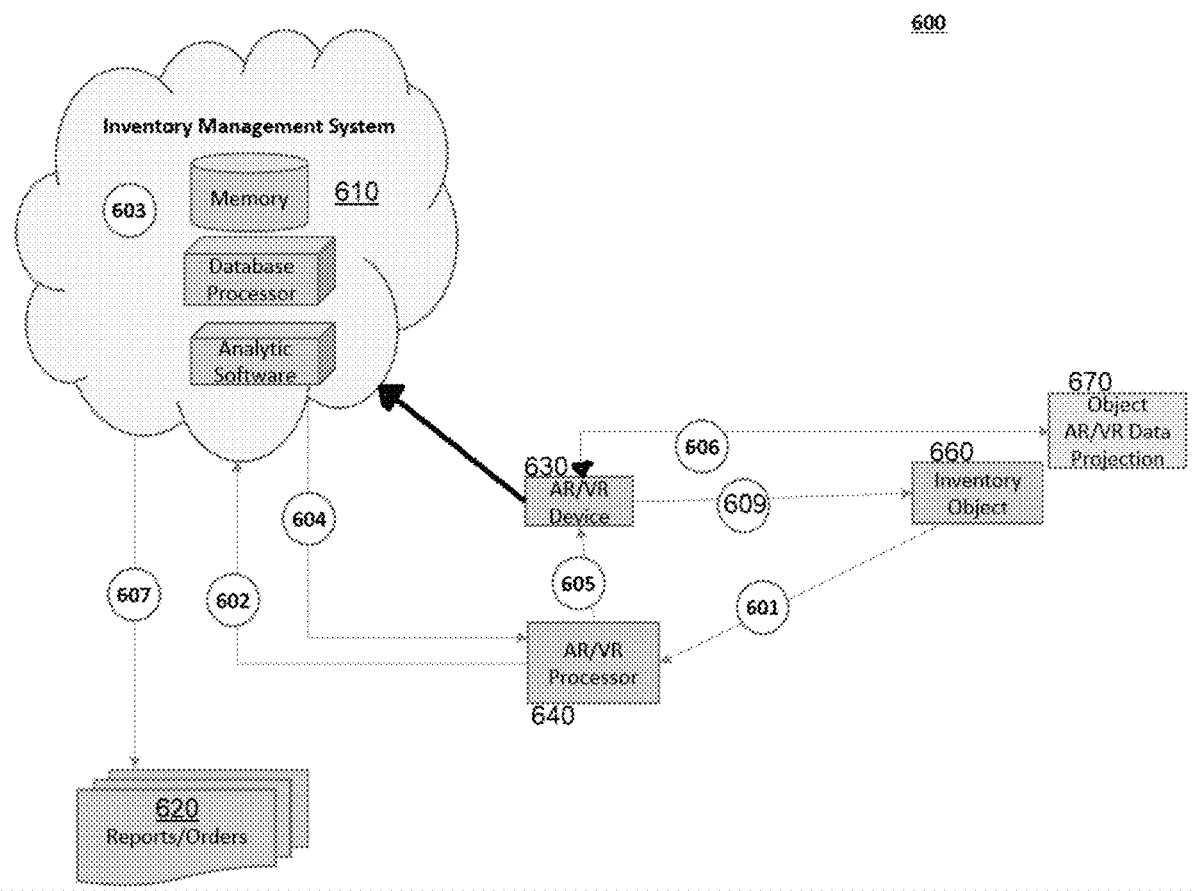
FIG. 6 is a technical environment into which a workflow has been integrated in order to illustrate some aspects of some embodiments of the present invention.

FIG. 6 is a technical environment 600 into which a workflow has been integrated in order to illustrate some aspects of some embodiments of the present invention. In this example, program code executing certain of the aspects of the invention executes on a processor of an AR/VR device 640. As illustrated in FIG. 6, because embodiments of the present invention include an API or other interfacing software/hardware (e.g., middleware), the program code of embodiments of the present invention provides a communication interface between an inventory management system 610 and an AR/VR device 630, such that various proprietary and third party inventory management systems 610 and/or AR/VR devices 630 can be utilized to perform aspects of some embodiments of the present invention. For example, inventory management systems utilized in embodiments of the present invention can include, but are not limited to, WAN-based, LAN-based, and/or cloud-based computing resources. For illustrative purposes, the exemplary inventory management system 610 of FIG. 3 is a cloud computing system and includes resources such as a memory, a database processor, and/or analytical software.

In some embodiments of the present invention, a user wearing an AR/VR device 630, or otherwise utilizing it, perceives, in the user's field of view, and, therefore, within a field of perception of the AR/VR device 630, an inventory object 660 (609). The program code executing on the processor of the AR/VR device 640 obtains readable indicia (e.g., FIG. 5) from the inventory object 660 (609) and identifies the inventory object 660 (601), based on the indicia. To identify the inventory object 660, based in the indicia interpreted by the program code (601), the program code executing on the processor of the AR/VR device 640 queries the inventory management system 610 (602) and responsive to the query, which includes the indicia (including decoded indicia if the indicia was encoded), obtains additional data related to the inventory object 660 (604). For example, utilizing the example of the trays discussed earlier, responsive to identifying the object, the inventory object 660 can provide the user with images that represent layers of a kit (assuming in this example that the kit is the identified inventory object 660). The data can also include recall information and/or data related to the amount of the inventory object 660 at a given location and/or at a variety of locations. The data can also include statistical data related to the inventory object 660. The program code executing on the processor of the AR/VR device 640 provides the additional data from the inventory management system 610 to the AR/VR device 640 (605). The AR/VR device 640 generate a data projection 670 of both the object itself (either keeping the object in the viewer and/or producing an enhanced image based on the additional data) and within the same view, provides the additional data. Thus, the (augmented reality and/or virtual reality) device 640 provides a composite view to the user. In some embodiments of the present invention, the composite view includes a three dimensional image of the object 660 and data related to the object 660, including but not limited to, inventory count, and/or expiration date. The program code can display the object 660 and/or the item utilization and or data related to the item on the augmented/ virtual reality device 640. The one or more programs can also generate a visualization which includes the data associated with the object or objects displayed in augmented/ virtual reality space, where the subject object or objects resides as observed by the user. In some embodiments of the present invention, based on the type of data, the program code can determine where/how it is visualized to the user.

Utilizing an interface provided by the AR/VR device 640 (and/or communicatively coupled to the AR/VR device 640), the user provides input, based on the projection 670. Based on interacting with the projection 670, the user experience can feel like the user is providing input in the projection, while it is devices with interfaces that obtain inputs and translate those inputs into commands (providing feedback to the program code). For example, a user wearing an IoT device with a motion sensor can provide inputs to the AR/VR device 640, via the IoT device, based on the IoT device providing motion data to the AR/VR device 640. As understood by one of skill in the art, the projection itself is not necessarily an interface (although it can be if provided on a handheld in two or three dimensions), but the motions of the user can create inputs as well as the speech of the user. Additionally, the AR/VR device itself can include monitors that interpret physical motions, including eye movements, as inputs. As discussed above, these interfaces are available as part of the AR/VR device 640. The AR/VR device 640 translates obtained inputs from the user and provides them to the inventory management system 610 (603). Thus, based on these inputs (based on the projection), the program code triggers the inventory management system 610 to automatically generate, in accordance with the inputs of the user, one or more of reports, related to the inventory object 660 and/or order for replenishment or return of the inventory object 660. Generating an order is one of a number of actions that the program code can take in embodiments of the present invention. In embodiments of the present invention, based on the input of the user, the program code can automatically complete or initiate a variety of tasks, including but not limited to: 1) generating an order request for an item represented in the AR/VR simulation/visualization created by the program code executing on the device; 2) counting inventory for an item represented in the AR/VR simulation/ visualization created by the program code executing on the device; 3) triggering a recall of an item represented in the AR/VR simulation/visualization created by the program code executing on the device; and/or 4) triggering a search in the one or more designated databases for additional data to supplement the descriptive text (generated by the program code and also displayed in the interface) related to an item represented in the AR/VR simulation/visualization created by the program code executing on the device.

In addition to the general workflow described above, FIG. 6 also illustrates a workflow where the object 660 is more than one item. Returning, to FIG. 6, one or more programs executing on the processor 640, obtains a signal of decodable indicia from an inventory object 660 (609). The one or more programs (also referred to as program code) decode the signal of decodable indicia to access decoded data (601). The decoded data includes information identifying the object 660. Although the singular, object 660, in used, the object can include a plurality of items. The one or more programs then obtain, either from the memory of the processor 640 and/or an inventory management system 610 communicatively coupled to the processor, a visual representation of a portion of the object 660 (602) (604). The one or more programs displays the augmented/virtual reality visual representation of the object 660 (606). In some embodiments of the present invention, the program code displays the visual representation in three dimensions. The visual representation can include a plurality of regions and each region represents an item of the plurality of items (keeping in mind that the object 660 itself is made up of more than one item, in this non-limiting example). The visual can be either two or three dimensional. Through a user interface of the AR/VR device 630, which the one or more programs are utilizing to display the visual representation, the one or more programs obtain a designation of at least one of the plurality of regions (606). The one or more programs in some embodiments of the present invention, based on obtaining the designation, generates an order request for an item represented by the designated region (607). In some embodiments of the present invention, the one or more programs make this request through the inventory management system 610. As discussed above, generating an order is only one example of actions that can be taken by the program code in embodiments of the present invention based on inputs by the user.

Figure 7:
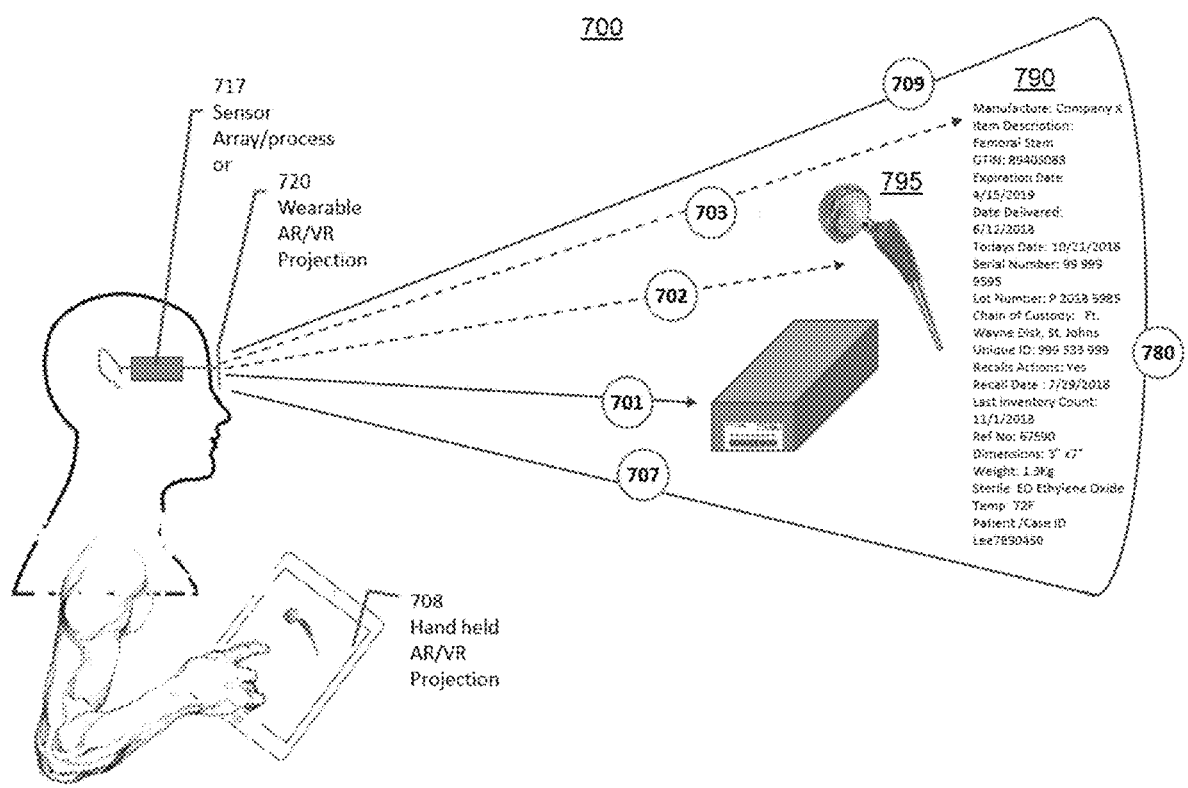
FIG. 7 is an example of a composite image (also referred to as a data visualization and/or projection) produced by program code in some embodiments of the present invention.

Because embodiments of the present invention provide visual feedback to users in real-time, in some embodiments of the present invention, based on generating the order (or taking another action), the program code updates the data projection 670 to reflect the change (based on the order or other action). Referring to FIG. 7, which will be discussed in greater detail, as a composite image comprising the projection 780 (e.g., FIG. 6, 670), includes an image 795 of the object and data describing the object, presented as text 790, in some embodiments of the present invention, based on the action, the program code can update the text 790 to show the pending change in inventory that is a results of the action. For example, if the action were an order, the program code would update the inventory. If the action were a recall request, the program code could update the expiration of the item.

As mentioned briefly above, FIG. 7 is an example of a composite image 780 (also referred to as a data visualization and/or projection) produced by program code executing on one or more processors in some embodiments of the present invention. As illustrated in FIG. 7, the program code obtains various indicia (e.g., 709, 703, 702, 701, 707, which are also depicted as example with similar numbering in FIG. 5) via a AR/VR device that includes an element capable of a projection 720 into three dimensional space and a sensor array/processor 717, to obtain and interpret the indicia (in order to potentially pull additional data from an inventory management system and/or other data sources with which the device can communicate over a communications connection). The program code executing on the processor 717 generates the visual representation, which can include one or more of a projection 780 into three dimensional space and/or a representation on a handheld device 708. In some embodiments of the present invention, a user interacts with and manipulates the projection 780 by interacting with interfaces, including but not limited to, a touchscreen, of the handheld device 708. As illustrated in FIG. 7, the visual generated by the program code that appears as a projection to the user, due to the AR/VR device functionality, includes the image of the object 795 and data associated with the object 790. The program code obtains the data in real-time. In some embodiments of the present invention, the image of the object 795 is captured by the program code when the program code obtains the indicia, but in some embodiments of the present invention, the image is retained and obtained, based on the indicia.

Returning to FIG. 6, in some embodiments of the present invention, the program code obtains images from an inventory management system 610, to utilize when generating the composite image (e.g., FIG. 7, 780). In some embodiments of the present invention, either the inventory management system 610 and/or the AR/VR processor 640 includes back-end data, the enables the user, through an interface, to make an image-based selection for inventory management (606) (603). The back-end data includes, in some embodiments of the present invention, meta-data and data, which include product and scheduling data, as well as kit layer information for processing kits. Although this data can be stored on a server, or in a centralized database, including in the resources of the inventory management system 610, the program code executing on the AR/VR device, can request a data synchronization to transfer the meta-data from the data manager to a memory resource local to the device. The data synchronization enables the mobile application to operate in environments without an easily accessible communications connection.

As discussed above, the example of replenishing items in a collection is helpful in illustrating certain functionality of the present invention. Thus, this non-limiting example is returned to and illustrated in FIG. 8. In some embodiments of the present invention, functionality related to the visual kit inventory described utilizes on meta-data. When using the visual scanning feature for kits, the meta-data supporting this operation includes, but is not limited to data definitions pertaining to: kit information, kit layer information, and layer products. Kit Information is data specific to a kit itself and includes, but is not limited to, SKU numbers, kit aliases, descriptions, lot codes, and the number of layers present within the kit. Kit Layer Information includes kit layer meta-data which includes the high-resolution images of the kit and information designating which layer each image pertains to (e.g., First/top, second, etc.). Layer Products meta-data provides the product ID and product information for each product present on the kit layer. As will be understood by one of skill in the art, although the product utilized in the examples given is a medical kit commonly utilized in an OR, the techniques of the present invention can be applied to any items and are especially helpful when the inventory is kept in layers in a given container, like, for example, a tool case.

Figure 8:
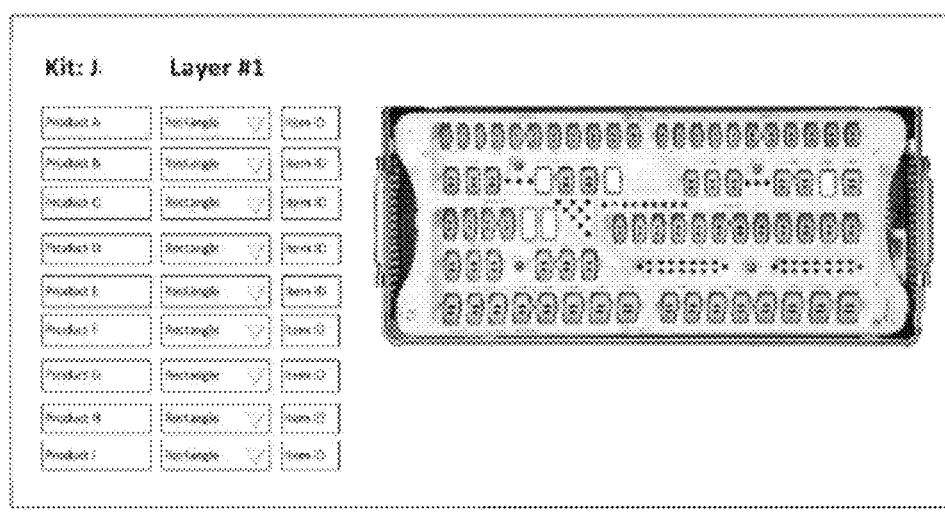
FIG. 8 is an illustration of some aspects of certain embodiments of the present invention.

FIG. 8 is an example of a kit, but displayed in two dimensions, for ease of understanding, though embodiments of the present invention can generate the display of FIG. 8 in three dimensions as well as in two dimensions. As seen in FIG. 8, once the kit layers, images and products have been obtained, the program code can create the coordinate points/shapes for each product location on each image. Thus, returning to FIG. 7, the composite image 780 displayed by the program code can include the detail provided by the metadata and the image resources.

Referring to FIG. 8, in an embodiment of the present invention, while the program code is scanning products and/or otherwise obtaining the indicia, the data is retrieved from the database utilizing the services layers. In an embodiment of the present technique, if the product scanned in a kit and the kit may be opened to audit, the system will load the associated image for the kit and layer. The user may navigate between layers of a kit by interacting with a virtual reproduction of the whole kit and/or the individual layers. As aforementioned, the three dimensional view generated by and augmented/virtual reality device provides the user with a three dimensional view of the kit, but for ease of use, the device may render each layer separately and enable the user to interact with one layer at a time. When utilizing an augmented reality device to view the kit and the layers, the user may alternative between layers by making pre-determined inputs into an I/O device that is communicatively coupled to the augmented reality device. When using a virtual reality device, the user may move between various layers and/or interact with the kit as a whole, by using movements and/or voice commands. The device may provide haptic feedback to the user to indicate the acceptance of the inputs.

Once a user has made a selection, an auditor can compare the picture on the screen and select items that are not present on the kit layer. This will cause the item to "Gray Out" or otherwise highlight the image. Once the inventory has been completed for the kit, the program code determines which products are present (and those that are not) and builds the inventory list for the kit. In some embodiments of the present invention, the actions of the auditor are accomplished automatically by the program code.

The program code produces a picture of an item upon obtaining a barcode and/or other indicia, decoding the indicia, and determining that it represents a kit comprised of trays. Upon viewing a three dimensional representation of the image (generated by an augmented reality or virtual reality device), a user can compare the rendering of a full tray, with the actual tray s/he is examining. When the user locates empty areas in the actual tray, the user can select the missing items either through a GUI and/or based on making movements and/or voice commands. The user can select and highlight areas where items are missing. The program code receives these selections and creates a record of missing items for transmission to the server so that the data manager can create a replenishment order. Upon receipt of the selections, the virtual or augmented reality device may provide the user with haptic feedback.

As illustrated in FIG. 7, in an embodiments of the present invention, the virtual reality device or the augmented reality device utilized to render the three dimensional views 795 of the products may also display the product information 790 to the user. Thus, a user need not be knowledgeable about the products initially and can view this information as s/he is making a selection. In some embodiments of the present invention, when a selection is made, the device may display the information about the product selected (as retrieved from the database) such that the user has the opportunity to review and/or confirm an item selected. Thus, in some embodiments of the present invention, the product information 790 (FIG.

7) would appear as part of a composite image, including in the image example of FIG. 8.

For example, in embodiments of the present invention, the program code, based on obtaining the designation (e.g., of a region in FIG. 8), can generate an order request. However, the program code can also log inventory data for reporting and acquire data relating to the expirations and or patient/case number for an item represented by the at least one of the plurality of regions. The program code can store the data acquired to memory or display the data in an AR/VR environment by interfacing with inventory management system and/or readable indicia. The data displayed can include, but is not limited to, manufacture, item description, GTIN, expiration date, date delivered, current inventory date and count, last inventory date and count, product family, serial number, lot number, chain of custody, location, unique ID, recall/field actions, recall date, reference number, dimensional data, weight/mass, sterilization method, temperature and patient/case ID and/or other electronic medical record (EMR) identifier. In some embodiments of the present invention, as demonstrated in FIG. 7, the program code can visually overlay the information on an image of a surgical kit, such as that displayed in FIG. 8, as the surgical kit contains implants, surgical instruments, sterilization process department to visually align or using other readable indicia medical supply contents with assigned storage location compartments within kits or other storage devices.

In embodiments of the present invention, a device utilized by a user to obtain identifiable information regarding an object can utilize various techniques to obtain data utilized to identify the object efficiently. The device may utilize a single view of multiple objects to capture barcodes and/or other indicia. The device may also read verbiage on containers, in cases where barcodes may be damaged. The device may also capture information in real-time. The device may be utilized to recognize an object based on its silhouette and other form factors of its images. As discussed in FIG. 1, the device, in some embodiments of the present invention, reads indicia broadcasting information throughout the electromagnetic spectrum, including but not limited to RFID, NFC, Passive Wi-Fi, Wi-Fi, UHF, and/or VHF spectrum technologies.

In embodiments of the present invention where the augmented or virtual reality device displays one tray at a time (or in other areas, sub-images and comprise a full image of an item), upon completing an analysis of one tray, utilizing the augmented reality or virtual reality device, the program code can render the next tray in the given kit. Just as with the first tray, the user can select areas to represent missing items and thus, enable the program code that comprises the data manager to create a replenishment order for the missing items (e.g., FIG. 6, 607).

Items related to the medical industry are merely offered as examples of how notes features of the present system work. As will be understood by one of skill in the art, the systems and methods disclosed herein are applicable across inventory management systems in a variety of industries, including for example retail merchandise, automotive, food service, etc.

Embodiments of the present invention can be utilized to manage the inventory in an operating room (OR), for example, for inventory management. Embodiments of the present invention may be utilized to capture consumption of materials in the OR at time of completion of the OR procedure or case. A qualified user in the OR setting, including but not limited to a Sales Rep., and/or an OR Nurse, may use this functionality to capture inventory consumed during a surgical procedure. By capturing inventory use during a surgical procedure, a full-cycle count during each service event is no longer needed to track the inventory. By utilizing this functionality, a full cycle (physical) count can occur less frequently, for example, as a monthly event or a quarterly event, with a reconciliation capability built in.

In an embodiment of the present invention, the GUI used for OR Inventory Management includes an input (such as a button rendered on a screen), to enable a user to make an entry. Because of the time constraints of users working in an OR, an embodiment of the present invention utilizes the aforementioned memory resources to pre-populate data by matching on data entries by the user. Information collected for a given surgery may include, but is not limited to: Date/Time of surgery, Patient unique ID (to protect the privacy and comply with privacy regulations, embodiments of the present invention will not track patient-specific data that would enable individuals using the system to identify the patients), Surgeon Name, Sales Rep Name, Sales Rep ID, Manufacturer Utilized (OEM), Provider Location (may be inclusive of all locations to a particular chain). Product information tracked within an embodiment of the present invention may include, but is not limited to: Product ID, Product Name and Description, and Quantity.

In an embodiment of the present invention, a user may identify which products are consumed in an OR setting (or any setting) by utilizing visuals (including augmented or virtual representations) of the kits displayed by the invention. This aspect was discussed earlier, however, in an embodiment of the present invention, a user may utilize this feature to replenish items used in an OR setting by interacting with and/or experiencing a three dimensional rendering to select products used from a kit (including via gestures, inputs through a GUI, and/or voice commands). As discussed earlier, all products visually selected may be added to a consumption list by the present system and method. Other features of the present invention include, but are not limited to, a search feature enabling a user to search for kits (or other products) by keyword, name or product id, a select feature that enables a user to select item on picture, wherein the software will obtain the selection and display information about the selected product, including but not limited to ID, Name, Description and/or Quantity.

Benefits of utilizing the described system and method for inventorying commercial products, including but not limited to, sterile packed healthcare products, include: 1) increasing speed by significantly reducing the auditor's time investment in securing the critical information contained in the bar codes located on the outside of the implant boxes; 2) increasing accuracy by reducing human error introduced when scanning an individual box is accidentally skipped by an auditor; and 3) increasing the ability of a user to perceive, fully, all pertinent information about a product, in a comprehensive view that does not interfere with other activities the user is engaged in at the time.

As discussed earlier, a benefit of embodiments of the present invention, is that it presents users with a faster and more efficient way to enter and locate information to assist the user in inventory management. Below are some examples of areas in which embodiments of the present invention may be utilized.

Healthcare Areas of Use:
Total Joints
Trauma
SPD
Cranial Maxio Facial
Interventional Radiology Cardio CRM
Electronic Medical Records—At time of input in the OR
Dental
Spine
MedSurge
Ocular
Pharmaceuticals
Hospital Supplies—Consumables
Physical Locations of Use:
Acute Care Facilities
Surgery Centers
Physician Offices
Home Healthcare
Distribution and Warehouse Centers for Healthcare products, Implants and Supplies
Medical Implant/Device Manufactures
Pharmacies Because of the user of augmented and/or virtual reality in embodiments of the present invention, embodiments of the present invention provide a number of benefits to users in the area of inventory management. For example, various embodiments of the present invention can utilize a variety of off-the-shelf augmented reality and virtual reality devices, including many wearable devices that are hands-free when worn. Utilizing a hands-free device to view inventory-related images and/or to interact with these images to replenish supplies, through body movements and/or voice commands, allows described aspects of the invention to operate in a hands-free work environment. In surgical environments, such as the OR, where keeping areas sterile is of a prime concern, utilizing hands-free functionality assists in preserving the environment and eliminates certain risks presented when a user must make inputs into a device with the user's hands, as it is possible that both the device receiving the inputs and the user's hands are not sanitary. In addition to being sanitary, a wearable device enables the mobility of the user, such that the user can physically navigate various areas in the environment in which s/he is using the device. Other advantages of utilizing a wearable device include, but are not limited to: comfort, durability, speed of input, and accuracy of input. Utilizing augmented reality and virtual reality technologies that enable ease of interaction with the software, as the multi-modal interface provides for intuitive inputs and minimized the requirement of product knowledge.

Embodiments of the present invention include a computer-implemented method, a computer program product, and a system, where program code executing on one or more processors obtains a signal of decodable indicia and decodes the signal of decodable indicia to access decoded data, where the decoded data comprises information identifying an object, where the object comprises a plurality of items. Based on the information identifying the object, the program code obtain, from a memory, a visual representation of a portion of the object, where the visual representation is divided into a plurality of regions and each region represents an item of the plurality of items. Based on identifying the object, the program code obtains data comprising descriptive text characterizing the portion of the object, where the descriptive text comprises quantitative inventory data related to the portion of the object. The program code displays the visual representation as a three dimensional image and the descriptive text, via a device, wherein the device is selected from the group consisting of: an augmented reality device and a virtual reality device, where the three dimensional image comprises a virtual projection in three dimensional space in a range of view of a user utilizing the device, where the device comprises a user interface. The program code obtains, via the user interface, a designation of at least one of the plurality of regions in the visual representation. Based on obtaining the designation, the program code executes an action, where the action changes a quantitative or a qualitative element of the descriptive text for an item represented by the at least one of the plurality of regions. The program code updates, concurrently with the executing, the descriptive text in the visual representation to reflect the changed quantitative or qualitative element.

In some embodiments of the present invention, the action comprises generating an order request for the item represented by the at least one of the plurality of regions, and wherein the updating comprises the descriptive text in the visual representation to reflect a change in the quantitative inventory data, based on the request for the order.

In some embodiments of the present invention, the action is selected from the group consisting of: counting inventory for the item represented by the at least one of the plurality of regions in one or more designated databases communicatively coupled to the one or more processors, triggering a recall of the item, triggering a search in the one or more designated databases for additional data to supplement the descriptive text related to the item, and generating an order request for the item.

In some embodiments of the present invention, the action comprises counting the inventory for the item represented by the at least one of the plurality of regions in the one or more designated databases communicatively coupled to the one or more processors, and the action further comprises the program code comparing results of the counting to a number of the items in inventory at a previous time.

In some embodiments of the present invention, the interface is selected from the group consisting of: a haptic feedback interface, a voice recognition interface, an audio interface, a gesture recognition interface, and a biometric recognition interface.

In some embodiments of the present invention, based on obtaining the designation, the program code updates the displaying of the visual representation to visually differentiate the at least one of the plurality of regions from other regions of the plurality of regions.

In some embodiments of the present invention, the three dimensional image comprises the portion of the object, as perceived by the user, in three dimensional space.

In some embodiments of the present invention, the descriptive text is displayed as a virtual overlay on the object.

In some embodiments of the present invention, the program code obtains, from the memory, a visual representation of a second portion of the object, where the visual representation of the second portion is divided into a plurality of regions and each region represents an item of the plurality of items, and where the second portion does not contain items of the plurality of items in the portion. The program code updates the three dimensional image to include the visual representation of the second portion on the client. The program code obtains a second designation, the second designation comprising a selection of at least one of the plurality of regions of the visual representation of the second portion. Based on obtaining the second designation, the program code updates the order request to include a request for an item represented by the at least one of the plurality of regions of the visual representation of the second portion; and the program code updates, concurrently with the generating, the descriptive text in the visual representation to reflect a change in the quantitative inventory data, based on the updated request for the order.

In some embodiments of the present invention, obtaining the signal of decodable indicia and the decoding the signals is executed by the device.

In some embodiments of the present invention, the device is further selected from the group consisting of a wearable device, and implanted device, a handheld device, and a stationary device.

In some embodiments of the present invention, the program code generates a report based on the updated descriptive text.

In some embodiments of the present invention, the descriptive text includes an element selected from the group consisting of: expiration date, identifier, name, description, and quantity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A computer-implemented method, the method comprising:
   obtaining, by one or more processors, a signal of decodable indicia;
   decoding, by the one or more processors, the signal of decodable indicia to access decoded data, wherein the decoded data comprises information identifying an object, wherein the object comprises a plurality of items;
   based on the information identifying the object, obtaining, by the one or more processors, from a memory, a visual representation of a portion of the object, wherein the visual representation is divided into a plurality of regions and each region represents an item of the plurality of items;
   based on identifying the object, obtaining, by the one or more processors, data comprising descriptive text characterizing the portion of the object, wherein the descriptive text comprises quantitative inventory data related to the portion of the object;
   displaying, by the one or more processors, the visual representation as a three dimensional image and the descriptive text, via a device, wherein the device is selected from the group consisting of: an augmented reality device and a virtual reality device, wherein the three dimensional image comprises a virtual projection in three dimensional space in a range of view of a user utilizing the device, wherein the device comprises a user interface;
   obtaining, by the one or more processors, via the user interface, a designation of at least one of the plurality of regions in the visual representation;
   based on obtaining the designation, executing an action, wherein the action changes a quantitative or a qualitative element of the descriptive text for an item represented by the at least one of the plurality of regions, wherein the action comprises generating an order request for the item represented by the at least one of the plurality of regions, and wherein the updating comprises updating the descriptive text in the visual representation to reflect a change in the quantitative inventory data, based on the request for the order;
   updating, by the one or more processors, concurrently with the executing, the descriptive text in the visual representation to reflect the changed quantitative or qualitative element;
   obtaining, by the one or more processors, from the memory, a visual representation of a second portion of the object, wherein the visual representation of the second portion is divided into a plurality of regions and each region represents an item of the plurality of items, and wherein the second portion does not contain items of the plurality of items in the portion;
   updating, by the one or more processors, the three dimensional image to include the visual representation of the second portion on the client;
   obtaining, by the one or more processors, a second designation, the second designation comprising a selection of at least one of the plurality of regions of the visual representation of the second portion;
   based on obtaining the second designation, updating, by the one or more processors, the order request to include a request for an item represented by the at least one of the plurality of regions of the visual representation of the second portion; and
   updating, by the one or more processors, concurrently with the generating, the descriptive text in the visual representation to reflect a change in the quantitative inventory data, based on the updated request for the order.

2. The computer-implemented method of claim 1, wherein the action further comprises an additional action selected from the group consisting of: counting inventory for the item represented by the at least one of the plurality of regions in one or more designated databases communicatively coupled to the one or more processors, triggering a recall of the item, and triggering a search in the one or more designated databases for additional data to supplement the descriptive text related to the item.

3. The computer-implemented method of claim 2, wherein the additional action comprises counting the inventory for the item represented by the at least one of the plurality of regions in the one or more designated databases communicatively coupled to the one or more processors, and the action further comprises comparing, by the one or more processors, results of the counting to a number of the items in inventory at a previous time.

4. The computer-implemented method of claim 1, wherein the interface is selected from the group consisting of: a haptic feedback interface, a voice recognition interface, an audio interface, a gesture recognition interface, and a biometric recognition interface.

5. The computer-implemented method of claim 1, further comprising:
based on obtaining the designation, updating, by the one or more processors, the displaying of the visual representation to visually differentiate the at least one of the plurality of regions from other regions of the plurality of regions.

6. The computer-implemented method of claim 1, wherein the three dimensional image comprises the portion of the object, as perceived by the user, in three dimensional space.

7. The computer-implemented method of claim 6, wherein the descriptive text is displayed as a virtual overlay on the object.

8. The computer-implemented method of claim 1, wherein the obtaining the signal of decodable indicia and the decoding the signals is executed by the device.

9. The computer-implemented method of claim 1, wherein the device is further selected from the group consisting of a wearable device, and implanted device, a hand-held device, and a stationary device.

10. The computer-implemented method of claim 1, further comprising: generating, by the one or more processors, a report based on the updated descriptive text.

11. The computer-implemented method of claim 1, wherein the descriptive text includes an element selected from the group consisting of: expiration date, identifier, name, description, and quantity.

12. A computer program product comprising:
a computer readable storage medium readable by one or more processors and storing instructions for execution by the one or more processors for performing a method comprising:
obtaining, by the one or more processors, a signal of decodable indicia;
decoding, by the one or more processors, the signal of decodable indicia to access decoded data, wherein the decoded data comprises information identifying an object, wherein the object comprises a plurality of items;
based on the information identifying the object, obtaining, by the one or more processors, from a memory, a visual representation of a portion of the object, wherein the visual representation is divided into a plurality of regions and each region represents an item of the plurality of items;
based on identifying the object, obtaining, by the one or more processors, data comprising descriptive text characterizing the portion of the object, wherein the descriptive text comprises quantitative inventory data related to the portion of the object;
displaying, by the one or more processors, the visual representation as a three dimensional image and the descriptive text, via a device, wherein the device is selected from the group consisting of: an augmented reality device and a virtual reality device, wherein the three dimensional image comprises a virtual projection in three dimensional space in a range of view of a user utilizing the device, wherein the device comprises a user interface;
obtaining, by the one or more processors, via the user interface, a designation of at least one of the plurality of regions in the visual representation;
based on obtaining the designation, executing an action, wherein the action changes a quantitative or a qualitative element of the descriptive text for an item represented by the at least one of the plurality of regions, wherein the action comprises generating an order request for the item represented by the at least one of the plurality of regions, and wherein the updating comprises updating the descriptive text in the visual representation to reflect a change in the quantitative inventory data, based on the request for the order;
updating, by the one or more processors, concurrently with the executing, the descriptive text in the visual representation to reflect the changed quantitative or qualitative element;
obtaining, by the one or more processors, from the memory, a visual representation of a second portion of the object, wherein the visual representation of the second portion is divided into a plurality of regions and each region represents an item of the plurality of items, and wherein the second portion does not contain items of the plurality of items in the portion;
updating, by the one or more processors, the three dimensional image to include the visual representation of the second portion on the client obtaining, by the one or more processors, a second designation, the second designation comprising a selection of at least one of the plurality of regions of the visual representation of the second portion;
based on obtaining the second designation, updating, by the one or more processors, the order request to include a request for an item represented by the at least one of the plurality of regions of the visual representation of the second portion; and
updating, by the one or more processors, concurrently with the generating, the descriptive text in the visual representation to reflect a change in the quantitative inventory data, based on the updated request for the order.

13. The computer program product of claim 12, wherein the action further comprises an additional action selected from the group consisting of: counting inventory for the item represented by the at least one of the plurality of regions in one or more designated databases communicatively coupled to the one or more processors, triggering a recall of the item, and triggering a search in the one or more designated databases for additional data to supplement the descriptive text related to the item.

14. The computer program product of claim 13, wherein the additional action comprises counting the inventory for the item represented by the at least one of the plurality of regions in the one or more designated databases communicatively coupled to the one or more processors, and the action further comprises comparing, by the one or more processors, results of the counting to a number of the items in inventory at a previous time.

15. The computer program product of claim 12, wherein the interface is selected from the group consisting of: a haptic feedback interface, a voice recognition interface, an audio interface, a gesture recognition interface, and a biometric recognition interface.

16. The computer program product of claim 12, further comprising:
based on obtaining the designation, updating, by the one or more processors, the displaying of the visual representation to visually differentiate the at least one of the plurality of regions from other regions of the plurality of regions.

17. A system comprising:
a memory;
one or more processors in communication with the memory;
a device selected from the group consisting of an augmented reality device and a virtual reality device, in communication with the one or more processors;
program instructions executable by the one or more processors via the memory to perform a method, the method comprising:
  obtaining, by the one or more processors, a signal of decodable indicia;
  decoding, by the one or more processors, the signal of decodable indicia to access decoded data, wherein the decoded data comprises information identifying an object, wherein the object comprises a plurality of items;
  based on the information identifying the object, obtaining, by the one or more processors, from the memory, a visual representation of a portion of the object, wherein the visual representation is divided into a plurality of regions and each region represents an item of the plurality of items;
  based on identifying the object, obtaining, by the one or more processors, data comprising descriptive text characterizing the portion of the object, wherein the descriptive text comprises quantitative inventory data related to the portion of the object;
  displaying, by the one or more processors, the visual representation as a three dimensional image and the descriptive text, via the device, wherein the three dimensional image comprises a virtual projection in three dimensional space in a range of view of a user utilizing the device, wherein the device comprises a user interface;
  obtaining, by the one or more processors, via the user interface, a designation of at least one of the plurality of regions in the visual representation;
  based on obtaining the designation, executing an action, wherein the action changes a quantitative or a qualitative element of the descriptive text for an item represented by the at least one of the plurality of regions, wherein the action comprises generating an order request for the item represented by the at least one of the plurality of regions, and wherein the updating comprises updating the descriptive text in the visual representation to reflect a change in the quantitative inventory data, based on the request for the order;
  updating, by the one or more processors, concurrently with the executing, the descriptive text in the visual representation to reflect the changed quantitative or qualitative element;
  obtaining, by the one or more processors, from the memory, a visual representation of a second portion of the object, wherein the visual representation of the second portion is divided into a plurality of regions and each region represents an item of the plurality of items, and wherein the second portion does not contain items of the plurality of items in the portion;
  updating, by the one or more processors, the three dimensional image to include the visual representation of the second portion on the client;
  obtaining, by the one or more processors, a second designation, the second designation comprising a selection of at least one of the plurality of regions of the visual representation of the second portion;
  based on obtaining the second designation, updating, by the one or more processors, the order request to include a request for an item represented by the at least one of the plurality of regions of the visual representation of the second portion; and
  updating, by the one or more processors, concurrently with the generating, the descriptive text in the visual representation to reflect a change in the quantitative inventory data, based on the updated request for the order.

* * * * *